United States Patent [19]

Roantree et al.

[11] 4,238,493

[45] Dec. 9, 1980

[54] 2-(SUBSTITUTED AMINO)-3-NITRO-2,3-UNSATURATED NITROGEN HETEROCYCLES

[75] Inventors: Michael L. Roantree, Welwyn Garden City; Rodney C. Young, Bengeo, both of England

[73] Assignee: Smith Kline & French Laboratories Limited, Welwyn Garden City, England

[21] Appl. No.: 43,785

[22] Filed: May 30, 1979

[30] Foreign Application Priority Data

May 30, 1978 [GB] United Kingdom ............... 24116/78

[51] Int. Cl.³ .................... A61K 31/415; A61K 31/44; C07D 401/12; C07D 403/12
[52] U.S. Cl. .................................... 424/263; 546/281; 546/256; 546/261; 424/273 R; 424/269; 424/270; 424/272; 424/274; 546/264; 546/278; 546/208; 548/336; 548/134; 548/136; 548/205; 548/214; 548/235; 548/247; 548/269; 260/244.4; 260/245.6; 260/326.9; 260/326.5 SM; 260/326.5 D; 544/322; 544/328
[58] Field of Search ............... 546/261, 264, 278, 281, 546/256; 424/263, 273 R; 548/336

[56] References Cited

U.S. PATENT DOCUMENTS

| 3,518,251 | 6/1970 | Gatzi | 546/264 |
|---|---|---|---|
| 3,932,644 | 1/1976 | Durant et al. | 424/263 |
| 3,953,460 | 4/1976 | Durant et al. | 424/273 |
| 3,980,781 | 9/1976 | Snell et al. | 424/251 |
| 4,128,658 | 12/1978 | Price et al. | 546/201 |
| 4,154,834 | 5/1979 | Brown et al. | 548/342 |

FOREIGN PATENT DOCUMENTS 1223686 3/1971 United Kingdom .

Primary Examiner—Alan L. Rotman
Assistant Examiner—Natalia Harkaway
Attorney, Agent, or Firm—Joan S. Keps; Richard D. Foggio; William H. Edgerton

[57] ABSTRACT 2,3-Unsaturated nitrogen-containing heterocyclic compounds with a 3-nitro group and a 2-heterocyclyl alkylamino group. The alkyl group of 2-position substituents is preferably interrupted by sulfur or oxygen. The compounds of the invention are preferably dihydropyrroles or tetrahydropyridines or pyrimidines. The compounds of the invention are histamine $H_2$-receptor antagonists.

9 Claims, No Drawings

2-(SUBSTITUTED AMINO)-3-NITRO-2,3-UNSATURATED NITROGEN HETEROCYCLES

This invention relates to nitro compounds having activity as histamine $H_2$-receptor antagonists, pharmaceutical compositions containing them and methods of inhibiting histamine $H_2$-receptors by administering these compounds.

Many physiologically active substances elicit their biological actions by interaction with specific sites known as receptors. Histamine is such a substance and it has multiple biological actions. Those biological actions of histamine which are inhibited by drugs commonly called "antihistamines", of which mepyramine, diphenhydramine and chlorpheniramine are typical examples, are mediated through histamine $H_1$-receptors. However, others of the biological actions of histamine are not inhibited by "antihistamines", and actions of this type which are inhibited by burimamide are mediated through receptors which are termed histamine $H_2$-receptors, and $H_2$-receptors are defined as those histamine receptors which are not blocked by mepyramine but are blocked by burimamide. Compounds which block histamine $H_2$-receptors are referred to as histamine $H_2$-receptor antagonists.

Blockade of histamine $H_2$-receptors is of value in inhibiting the biological actions of histamine which are not inhibited by "antihistamines". Histamine $H_2$-receptor antagonists are therefore useful, for example, as inhibitors of gastric acid secretion, as anti-inflammatory agents, and as agents which act on the cardiovascular system, for example as inhibitors of the effects of histamine on blood pressure.

The compounds of this invention are represented by Structure 1:

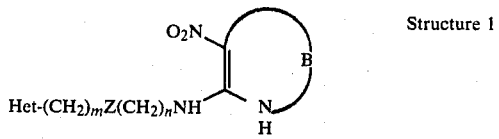

Structure 1 in which Het is either a 5- or 6-membered, fully-unsaturated heterocycle containing at least one nitrogen atom and optionally substituted by lower alkyl, trifluoromethyl, hydroxymethyl, halogen, hydroxy, lower alkoxy or amino, or a 5- membered fully-unsaturated heterocycle containing one oxygen or sulfur atom as the sole heteroatom, i.e. furyl or thienyl, and substituted by a group $R^1R^2N$-A- where $R^1$ and $R^2$, which can be the same or different, are each hydrogen, lower alkyl, $C_3$-$C_6$ cycloalkyl, lower alkenyl, aryl lower alkyl, lower alkyl substituted by lower alkoxy, (lower alkyl)amino or di(lower alkyl)amino, or $R^1$ and $R^2$ together with the nitrogen atom to which they are attached form a pyrrolidino or piperidine ring, and A is straight or branched $C_1$-$C_6$ alkanediyl group;

Z is sulphur, methylene or oxygen;

m is 0, 1 or 2 and n is 2 or 3 provided that m+n is 3 or 4; and B is a 1,2-ethanediyl (—$CH_2$—$CH_2$—), 1,3-propanediyl (—$CH_2CH_2CH_2$—) or 1,4-butanediyl (—$CH_2CH_2CH_2$—$CH_2$) group, which group is optionally substituted with one or more lower alkyl, aryl, aryl lower alkyl or heteroaryl lower alkyl groups, or B is a 2-aza-1,3-propanediyl group (—$CH_2NR^3CH_2$— where $R^3$ is lower alkyl, aryl, aryl lower alkyl or heteroaryl lower alkyl). The compounds of Structure 1 can be in the form of free bases or pharmaceutically acceptable acid addition salts thereof.

Herein, 'lower alkyl' and 'lower alkoxy' are used respectively to mean alkyl and alkoxy groups having 1 to 4 carbon atoms which can be straight or branched, and 'lower alkenyl' is used to mean alkenyl groups containing from 3 to 6 carbon atoms which can be straight or branched.

Examples of nitrogen-containing heterocycles for the group Het are imidazole, pyridine, thiazole, isothiazole, oxazole, isoxazole, 1,2,4-triazole, 1,2,5-thiadiazole and 1,3,4-thiadiazole. The group $(CH_2)_m$ is preferably linked to a carbon atom of the heterocycle adjacent to a nitrogen atom. The heterocycle of Het is preferably imidazole. In particular, Het can be 2- or 4-imidazolyl optionally substituted by lower alkyl (especially methyl), halogen (especially chlorine or bromine), trifluoromethyl or hydroxymethyl. Other suitable groups Het are 2-pyridyl optionally substituted by lower alkyl (especially methyl), lower alkoxy (especially methoxy), halogen (especially chlorine or bromine), amino or hydroxy; 2-thiazolyl; 3-isothiazolyl optionally substituted by chlorine or bromine; 3-(1,2,5-thiadiazolyl optionally substituted by chlorine or bromine; and 2-(5-amino-1,3,4-thiadiazolyl). Specific examples of groups Het are 5-methyl-4-imidazolyl, 5-bromo-4-imidazolyl, 3-bromo-2-pyridyl, 3-chloro-2-pyridyl, 3-methoxy-2-pyridyl and 3-hydroxy-2-pyridyl.

When Het is a 5- membered heterocycle containing one oxygen as the sole heteroatom(furyl), the group $(CH_2)_m$ is preferably linked to a carbon atom of the heterocycle adjacent to the oxygen atom. The group $R^1R^2N$-A- is preferably linked to the other carbon atom of the heterocycle adjacent to the hetero atom. $R^1$ and $R^2$ are preferably hydrogen, lower alkyl (especially methyl), phenyl(lower alkyl) where the phenyl group is optionally substituted by lower alkyl, lower alkoxy, halogen or di(lower alkyl)amino-(lower alkyl). A is preferably an $\alpha,\omega$-straight alkylene group containing from 1 to 3 carbon atoms, particularly methylene. Specific examples of such groups Het are 5-(4-dimethylamino)butyl)-2-furyl, 5-((dimethylamino)methyl)-2-furyl and 5-(methylaminomethyl)-2-furyl. Preferably Z is sulphur. Preferably m is 1 and n is 2.

Each carbon atom of B is preferably secondary or tertiary. The carbon atom of B adjacent to the ring nitrogen atom shown in Structure 1 is preferably unsubstituted. Examples of aryl substituents and the aryl moiety of aryl lower alkyl substituents for B are phenyl optionally substituted with one or more lower alkyl, lower alkoxy or halogen groups, particularly 3-methylphenyl, 3-methoxyphenyl, 3,4-dimethoxyphenyl and 3-chlorophenyl, 5- or 6- (2,3-dihydro-1,4-benzodioxinyl) and 4- or 5- (1,3-benzodioxolyl). Examples of heteroaryl substituents for B are 2-furyl, 2-thienyl, 2-pyridyl, 3-pyridyl or 4-pyridyl, which groups are optionally substituted by one or more lower alkyl or lower alkoxy groups, and particularly 3-pyridyl, 6-methyl-3-pyridyl and 6-methoxy-3-pyridyl.

Examples of specific compounds of the invention are:
2-[2-(5-methyl-4-imidazolylmethylthio)ethylamino]-3-nitro-1,4,5,6-tetrahydropyridine,
2-[2-(5-methyl-4-imidazolylmethylthio)ethylamino]-3-nitro-4,5-dihydropyrrole and
4[2-(5-methyl-4-imidazolylmethylthio)ethylamino]-5-nitro-1-benzyl-1,2,3,6-tetrahydropyrimidine.

The compounds of Structure 1 can be prepared by reacting a compound of formula Het-$(CH_2)_m$Y where Y is —$Z(CH_2)_n NH_2$ or optionally when m is 1 or 2 a leaving group displaceable by a mercaptan, for example halogen, trisubstituted phosphonium (for example triphenylphosphonium) or substituted sulphonyloxy (for example p-toluenesulphonyloxy, methanesulphonyloxy or trifluoromethanesulphonyloxy) with a compound of Structure 2:

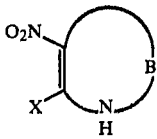

Structure 2 where X is halogen, QO- or QS (where Q is lower alkyl, aryl or arylalkyl, or another leaving group which is displaceable by an amine) when Y is —$Z(CH_2)_n NH_2$, and X is $HS(CH_2)_n NH$— when Y is a leaving group displaceable by a mercaptan. This reaction is preferably carried out in the presence of a solvent, for example a lower alkanol or pyridine. In general an elevated temperature will be used, for example the boiling point of the reaction mixture. The reaction can also be carried out in the absence of a solvent. X is preferably QS, in particular methylthio or benzylthio. It will be appreciated that when $R^1$ and/or $R^2$ are hydrogen or are lower alkyl substituted by (lower alkyl)amino it may be necessary to protect amino groups in the $R^1R^2N$-A-substituents of compounds of formula Het-$(CH_2)_m$Y to prevent competing side reactions.

The intermediate compounds of Structure 2 where X is QS-, and B is substituted or unsubstituted 1,2-ethanediyl, 1,3-propanediyl or 1,4-butanediyl group can be prepared by the following sequence of reactions. A compound of Structure 3

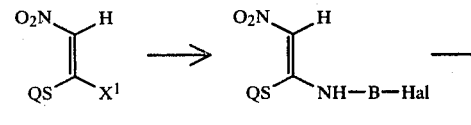

Structure 3    Structure 4

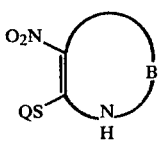

Structure 5 where $X^1$ is QS- or QSO-, is reacted with a compound of formula $H_2N$-B-Hal, where Hal is chlorine, bromine or iodine to give a compound of Structure 4. This reaction is preferably carried out in a solvent, for example a lower alkanol. Preferably Hal is bromine or iodine. The compounds of Structure 4 can be converted into a compound of Structure 5 by reaction with a strong base, for example sodium hydride or potassium t-butoxide. This reaction is preferably carried out in an inert polar solvent, for example tetrahydrofuran or dimethylformamide. In general an elevated temperature will be used, for example the boiling point of the reaction mixture.

An alternative method for preparing the intermediate compounds of Structure 2 where X is QS- and B is 1,2-ethanediyl or 1,3-propanediyl is to react a compound of Structure 3 with aziridine or azetidine or a C-substituted derivative thereof to give a compound of Structure 6

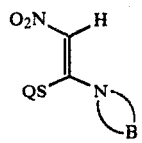

Structure 6 and to heat this compound in the presence of a catalyst, for example potassium iodide, to give a compound of Structure 5. The latter reaction is preferably carried out in a dry aprotic polar solvent, for example acetone or 2-butanone.

The intermediate compounds of Structure 2 where X is QS and B is 2-aza-1,3-propanediyl can be prepared by reacting a compound of Structure 7 with formaldehyde and an amine $R^3NH_2$.

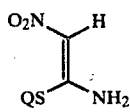

Structure 7

The compounds of Structure 7 can be prepared by reacting a compound of Structure 3 with ammonia.

The intermediate compounds of Structure 2 where X is $HS(CH_2)_n NH$- can be prepared by reacting a compound of Structure 2 (where X is a suitable leaving group displaceable by an amine) with an amine of formula $HS(CH_2)_n NH_2$.

The compounds of Structure 1 block histamine $H_2$-receptors; that is, they inhibit the biological actions of histamine which are not inhibited by "antihistamines" such as mepyramine but are inhibited by burimamide. For example, they inhibit histamine stimulated secretion of gastric acid from the lumen-perfused stomachs of rats anaesthetised with urethane, at doses of from 0.5 to 256 micromoles per kilogram intravenously. Their activity as histamine $H_2$-receptor antagonists is also demonstrated by their ability to inhibit other actions of histamine which are not mediated by histamine $H_1$-receptors. For example, they inhibit the actions of histamine on the isolated guinea pig atrium and isolated rat uterus. They inhibit the basal secretion of gastric acid and also that stimulated by pentagastrin or by food. In a conventional test such as the measurement of blood pressure in the anaesthetised cat, at doses of from 0.5 to 256 micromoles per kilogram intravenously, they inhibit the vasodilator action of histamine. The potency of the compounds is illustrated by an effective dose producing 50% inhibition of gastric acid secretion in the anaesthetised rat and 50% inhibition of histamine-induced tachycardia in the isolated guinea pig atrium (less than $10^{-4}$ Molar).

The pharmaceutical compositions of this invention comprise a pharmaceutical carrier and a compound of Structure 1 in the form of the free base or in the form of a pharmaceutically acceptable addition salt. Such addition salts include those with hydrochloric, hydrobromic, hydriodic, sulphuric and maleic acids, and their salts can conveniently be formed from the corresponding bases by standard procedures, for example by reacting the base with an acid in a lower alkanol or by the use of ion exchange resins to form the required salt either directly from the base or from a different addition salt.

The pharmaceutical carrier employed can be solid or liquid. Examples of solid carriers are lactose, terra alba, sucrose, talc, gelatin, agar, pectin, acacia, magnesium stearate and stearic acid. Examples of liquid carriers are syrup, peanut oil, olive oil and water.

If a solid carrier is used, the compositions can be prepared in the form of a tablet, capsule, troche or lozenge. The amount of solid carrier in a unit dosage form will generally be from about 25 mg to about 300 mg. If a liquid carrier is used, the compositions can be in the form of a syrup, emulsion, soft gelatin capsule, a sterile injectable liquid for example contained in an ampoule, or an aqueous or non-aqueous liquid suspension. The pharmaceutical compositions can be prepared by conventional techniques involving procedures such as mixing, granulating and compressing or dissolving the ingredients as appropriate to the desired form of composition.

The compositions of the present invention are preferably in dosage unit form each dosage unit containing an effective amount of active ingredient to block histamine $H_2$-receptors. Each dosage unit preferably contains the active ingredient in an amount of from about 50 mg to about 250 mg.

The invention provides a method of blocking histamine $H_2$-receptors which comprises administering to a subject an effective amount of a compound of Structure 1.

The active ingredient is preferably administered from one to six times per day. The daily dosage regimen will generally be from about 150 mg to about 1500 mg.

The route of administration can be oral or parenteral.

The invention is illustrated by the following Examples in which temperatures are in °C.

EXAMPLE 1

(a) A solution of sodium (0.09 g, 0.004 mol) in methanol (10 ml) was added dropwise to a stirred solution of 1-nitro-2-methylthio-2-methylsulphinyl-ethylene (0.5 g, 0.003 mol) and 3-bromopropylamine hydrobromide (0.9 g, 0.004 mol) in methanol (30 ml). The mixture was stirred for 5 hours, and then the solvent was removed in vacuo. The residue was dissolved in water (20 ml) and extracted with chloroform (2×30 ml). The extracts were combined, dried, and concentrated in vacuo. The solid residue was recrystallised from propan-2-ol to give 1-nitro-2-methylthio-2-(3-bromopropylamino)ethylene (0.3 g, 43%) m.p. 92°–92.5°.

Found: C, 28.2; H, 4.3; N, 10.9; S, 12.5; Br, 31.3; $C_6H_{11}BrN_2O_2S$. Requires: C, 28.2; H, 4.35; N, 11.0; S, 12.6; Br, 31.3%.

(b) A mixture of 1-nitro-2-methylthio-2-(3-bromopropylamino)ethylene (3.2 g, 0.012 mol) and sodium hydride (50% in oil, 0.9 g, 0.019 mol) in dry tetrahydrofuran (50 ml) was refluxed for 18 hours. The mixture was filtered, and the filtrate was evaporated to dryness. The residue was chromatographed on a silica gel column, the product being eluted with ethyl acetate. Recrystallisation of the product from methanol/propan-2-ol gave 2-methylthio-3-nitro-1,4,5,6-tetrahydropyridine (0.6 g, 29%) m.p. 230.5°–231.5°.

Found: C, 41.5; H, 5.7; N, 16.1; S, 18.25; $C_6H_{10}N_2O_2S$. Requires: C, 41.4; H, 5.8; N, 16.1; S, 18.4%.

(c) A solution of 2-(5-methyl-4-imidazolylmethylthio)ethylamine (0.51 g, 0.003 mol) and 2-methylthio-3-nitro-1,4,5,6-tetrahydropyridine (0.49 g, 0.003 mol) in ethanol (50 ml) was refluxed for 6 hours. The mixture was cooled, and the solvent was removed in vacuo. The residue was dissolved in hot propan-2-ol and the product crystallised on cooling. Recrystallisation of the product from propan-2-ol/methanol gave 2-[2-(5-methyl-4-imidazolylmethylthio)ethylamino]-3-nitro-1,4,5,6-tetrahydropyridine (0.66 g, 82%) m.p. 205.5°–206.5°.

Found: C, 48.6; H, 6.5; N, 23.6; S, 10.8; $C_{12}H_{19}N_5O_2S$. Requires: C, 48.5; H, 6.4; N, 23.55; S, 10.8%.

EXAMPLE 2

(a)(i) A solution of 1-nitro-2-methylthio-2-methylsulphinylethylene (2 g, 0.011 mol) and aziridine (0.5 g, 0.0116 mol) in methanol (20 mol) was stirred at room temperature for 1 hour. The solid which crystallised out was filtered off to give 1-nitro-2-methylthio-2-aziridinoethylene (1.3 g, 74%) m.p. 107.5°–110°. $^1H$ NMR ($CDCl_3$) δ:2.4 (S,4H, —$H_2CH_2$—), 2.56 (S, 3H, $CH_3$—) 7.15

(S, 1H, H )=.

(a)(ii) Nitrogen was passed for about 15 minutes through a solution of 1-nitro-2-methylthio-2-aziridinoethylene (0.5 g, 0.003 mol) in dry acetone (15 ml) and the solution was then warmed to 35°. Potassium iodide (2.5 g, 0.015 mol) was added to the solution, which resulted in the rapid formation of a heavy yellow precipitate. The solid was filtered off, washed with water and then with acetone to give 2-methylthio-3-nitro-4,5-dihydropyrrole (0.17 g, 34%) m.p. 207°–209°.

Found: C, 37.3; H, 4.9; N, 17.3; S, 19.75; $C_5H_8N_2O_2S$. Requires: C, 37.5; H, 5.0; N, 17.5; S, 20.0%.

(b)(i) A solution of sodium methoxide (sodium (0.3 g, 0.013 mol) in methanol (10 ml)) was added dropwise, over a period of 10 minutes to a stirred mixture of 1-nitro-2-methylthio-2-methylsulphinylethylene (2 g, 0.011 mol) and 2-bromoethylamine hydrobromide (2.7 g, 0.013 mol) in methanol (25 ml), cooled to 0°. The solution was stirred at 0° for a further 15 minutes, and then it was allowed to attain room temperature. After 1 hour, the solvent was removed in vacuo, and the semi-solid residue was extracted with hot chloroform (2×25 ml). The extracts were combined and concentrated in vacuo. The solid residue was recrystallised from propan-2-ol to give 1-nitro-2-methylthio-2-(2-bromoethylamino)ethylene (1.85 g, 71%) m.p. 123°14 126°.

Found: C, 25.1; H, 3.7; N, 11.8; S, 13.6; Br, 33.3; $C_5H_9BrN_2O_2S$. Requires: C, 24.9; H, 3.8; N, 11.6; S, 13.3; Br, 33.1%.

(b)(ii) A solution of 1-nitro-2-methylthio-2-(2-bromoethylamino)ethylene (3 g, 0.012 mol) and sodium hydride (50% in oil, 0.62 g, 0.013 mol) in dry tetrahydrofuran (100 ml) was refluxed for 7 hours. The reaction mixture was cooled, and the solvent was removed in vacuo. The residue was extracted with boiling ethyl acetate (2×50 ml), and the extracts were decolourized with charcoal. Concentration of the extracts in vacuo, followed by cooling, resulted in the crystallisation of 2-methylthio-3-nitro-4,5-dihydropyrrole (0.5 g, 26%).

(c) A solution of 2-(5-methyl-4-imidazolylmethylthio)ethylamine (1.3 g, 0.0076 mol) and 2-methylthio-3-nitro-4,5-dihydropyrrole (1.2 g, 0.0075 mol) in ethanol (50 ml) was refluxed for 1½hours. The mixture was cooled, and the solid was filtered off and recrystallised from methanol/water to give 2-[2-(5-methyl-4- imidazolylmethylthio)ethylamino]-3-nitro-4,5-dihydropyrrole (1.4 g, 66%) m.p. 207.5°–208°.

Found: C, 46.65; H, 6.15; N, 24.6; S, 11.5; $C_{11}H_{17}N_5O_2S$. Requires: C, 46.6; H, 6.05; N, 24.7; S, 11.3%.

EXAMPLE 3

(i) Aqueous ammonia (30% w/w, 9 ml, 0.16 mol) was added dropwise to a solution of 1-nitro-2-methylsulphinyl-2-methylthioethylene (20 g, 0.11 mol) in tetrahydrofuran (80 ml) at 50°. The mixture was stirred at 50° for 1 hour. The solvent was removed in vacuo, and the residue was chromatographed on a silica gel column. The product was eluted with petroleum ether (b.p. 60°–80°)/ethyl acetate (10:3) and recrystallised from ethyl acetate-petroleum ether to give 1-nitro-2-amino-2-methylthioethylene (1.5 g, 10%) m.p. 109°–110.5°.

Found: C, 27.1; H, 4.5; N, 20.7; S, 23.7; $C_3H_6N_2O_2S$. Requires: C, 26.9; H, 4.5; N, 20.9; S, 23.9%.

(ii) Formaldehyde (40% w/v, 2 ml, 0.03 mol) and benzylamine (3 ml, 0.03 mol) were successively added to a stirred solution of 1-nitro-2-amino-2-methylthioethylene (1 g, 0.007 mol) in methanol (20 ml). After 5 minutes, the solid was filtered off and recrystallised from methanol to give 1-benzyl-4-methylthio-5-nitro-1,2,3,6-tetrahydropyrimidine (1.3 g, 70%) m.p. 173°–173.5° C.

Found: C, 54.0; H, 5.6; N, 15.8; S, 11.8; $C_{12}H_{15}N_3O_2S$. Requires: C, 54.3; H, 5.7; N, 15.8; S, 12.1%.

(iii) A solution of 1-benzyl-4-methylthio-5-nitro-1,1,2,3,6-tetrahydropyrimidine (1 g, 0.004 mol) and 2-(5-methyl-4-imidazolylmethylthio)ethylamine (0.7 g, 0.004 mol) in methanol (40 ml) was heated, with stirring, at 60° for 10 hours. The solvent was removed in vacuo, and the residue was chromatographed on a silica-gel column. Ethyl acetate/propan-2ol (30%) eulted the product which was recrystallised from methanol-propan-2-ol to give 1-benzyl-4-[2-(5-methyl-4-imidazolylmethylthio)ethylamino]-5-nitro-1,2,3,6-tetrahydropyrimidine (0.5 g, 32%) m.p. 177°–180°.

Found: C, 55.5; H, 6.3; N, 21.4; S, 8.0; $C_{18}H_{24}N_6O_2S$. Requires: C, 55.65; H, 6.2; N, 21.6; S, 8.25%.

EXAMPLES 4 to 27

Substitution of an equivalent amount of
(a) 2-(2-imidazolylmethylthio)ethylamine
(b) 2-(4-imidazolylmethylthio)ethylamine
(c) 2-(5-bromo-4-imidazolylmethylthio)ethylamine
(d) 2-(5-trifluoromethyl-4-imidazolylmethylthio)ethylamine
(e) 2-(5-hydroxymethyl-4-imidazolylmethylthio)ethylamine
(f) 2-(2-pyridylmethylthio)ethylamine
(g) 2-(3-methyl-2-pyridylmethylthio)ethylamine
(h) 2-(3-methoxy-2-pyridylmethylthio)ethylamine
(i) 2-(3-chloro-2-pyridylmethylthio)ethylamine
(j) 2-(3-amino-2-pyridylmethylthio)ethylamine
(k) 2-(3-hydroxy-2-pyridylmethylthio)ethylamine
(l) 2-(3-isothiazolylmethylthio)ethylamine
(m) 2-(4-bromo-3-isothiazolylmethylthio)ethylamine
(n) 2-(3-(1,2,5)-thiadiazolymethylthio)ethylamine
(o) 2-(4-chloro-3-(1,2,5)-thiadiazolylmethylthio)-ethylamine
(p) 2-(5-amino-2-(1,3,4)-thiadiazolylmethylthio)-ethylamine
(q) 2-((5-(dimethylaminomethyl)2-furyl)methylthio)ethylamine
(r) 2-((5-(methylaminomethyl)-2-furyl)methylthio)ethylamine
(s) 2-((5-(1-pyrrolidinomethyl)-2-furyl)methylthio)ethylamine
(t) 2-((5-(methylethylaminomethyl)-2-furyl)methylthio)ethylamino
(u) 2-((5-dimethylaminomethyl)2-thienyl)methylthio)ethylamine
(v) 2-((5-(methylaminomethyl)-2-thienyl)methylthio)ethylamine
(w) 2-((5-(1-pyrrolidinomethyl)-2-thienyl)methylthio)ethylamine
(x) 2-((5-(methylethylaminomethyl)-2-thienyl)methylthio)ethylamino for 2-(5-methyl-4-imidazolylmethylthio)ethylamine in the procedure of Example 2 leads to the production of:

Example Number
4. 2-[2-(2-imidazolylmethylthio)ethylamino]-3-nitro-4,5-dihydropyrrole
5. 2-[2-(4-imidazolylmethylthio)ethylamino]-3-nitro-4,5-dihydropyrrole
6. 2-[2-(5-bromo-4-imidazolylmethylthio)ethylamino]-3-nitro-4,5-dihydropyrrole
7. 2-[2-(5-trifluoromethyl-4-imidazolylmethylthio)ethylamino]-3-nitro-4,5-dihydropyrrole
8. 2-[2-(5-hydroxymethyl-4-imidazolylmethylthio)ethylamino]-3-nitro-4,5-dihydropyrrole
9. 2-[2-(2-pyridylmethylthio)ethylamino]-3-nitro-4,5-dihydropyrrole
10. 2-[2-(3-methyl-2-pyridylmethylthio)ethylamino]-3-nitro-4,5-dihydropyrrole
11. 2-[2-(3-methoxy-2-pyridylmethylthio)ethylamino]-3-nitro-4,5-dihydropyrrole
12. 2-[2-(3-chloro-2-pyridylmethylthio)ethylamino]-3-nitro-4,5-dihydropyrrole
13. 2-[2-(3-amino-2-pyridylmethylthio)ethylamino]-3-nitro-4,5-dihydropyrrole
14. 2-[2-(3-hydroxy-2-pyridylmethylthio)ethylamino]-3-nitro-4,5-dihydropyrrole
15. 2-[2-(3-isothiazolylmethylthio)ethylamino]-3-nitro-4,5-dihydropyrrole
16. 2-[2-(4-bromo-3-isothiazolylmethylthio)ethylamino]-3-nitro-4,5-dihydropyrrole
17. 2-[2-(3-(1,2,5)-thiadiazolylmethylthio)ethylamino]-3-nitro-4,5-dihydropyrrole
18. 2-[2-(chloro-3-(1,2,5)-thiadiazolylmethylthio)ethylamino]-3-nitro-4,5-dihydropyrrole
19. 2-[2-(5-amino-2-(1,3,4)-thiadiazolylmethylthio)ethylamino]-3-nitro-4,5-dihydropyrrole
20. 2-[2-(5-(dimethylaminomethyl)-2-furylmethylthio)ethylamino]-3-nitro-4,5-dihydropyrrole
21. 2-[2-(5-(methylaminomethyl)-2-furylmethylthio)ethylamino]-3-nitro-4,5-dihydropyrrole 22. 2-[2-(5-(1-pyrrolidinomethyl)-2-furylmethylthio)ethylamino]-3-nitro-4,5-dihydropyrrole
23. 2-[2-(5-(methylethylaminomethyl)-2-furylmethylthio)ethylamino]-3-nitro-4,5-dihydropyrrole
24. 2-[2-(5-(dimethylaminomethyl)-2-thienylmethylthio)ethylamino]-3-nitro-4,5-dihydropyrrole
25. 2-[2-(5-(methylaminomethyl)-2-thienylmethylthio)ethylamino]-3-nitro-4,5-dihydropyrrole
26. 2-[2-(5-(1-pyrrolidinomethyl)-2-thienylmethylthio)ethylamino]-3-nitro-4,5-dihydropyrrole
27. 2-[2-(5-(methylethylaminomethyl)-2-thienylmethylthio)ethylamino]-3-nitro-4,5-dihydropyrrole Substitution of equivalent amounts of the above specified amines for 2-(5-methyl-4-imidazolylmethylthio)e- thylamine in the procedures of Example 1 and Example 3 leads to the production of the corresponding 2-[2-heterocyclylmethylthio)-ethylamino]-3-nitro-1,4,5,6-tetrahydropyridines and 1-benzyl-4-[2-(heterocyclylmethylthio)ethylamino]-5-nitro-1,2,3,6-tetrahydropyrimidines respectively.

EXAMPLES 28 to 31

Substitution of an equivalent amount of
(a) 4-(3-thiazolyl)butylamine,
(b) 4-(3-oxazolyl)butylamine,
(c) 4-(2-isoxazolyl)butylamine,
(d) 4-[3-(1,2,4-triazolyl)]butylamine,
for 2-(5-methyl-4-imidazolylmethylthio)ethylamine in the procedure of Example 2 leads to the production of Example Number 28. 2-[4-(3-thiazolyl)butylamino]-3-nitro-4,5-dihydropyrrole
29. 2-[4-(3-oxazolyl)butylamino]-3-nitro-4,5-dihydropyrrole
30. 2-[4-(2-isoxazolyl)butylamino]-3-nitrodihydropyrrole
31. 2-[4-(3-(1,2,4-triazolyl)butylamino]-3-nitrodihydropyrrole

EXAMPLE 32

Acid addition salts of the compounds of Examples 1 to 31 are prepared by reaction of the respective free bases with an appropriate acid. The hydrochlorides are prepared by reaction with hydrochloric acid, the reaction being effected in ethanol solution.

EXAMPLE 33

A pharmaceutical composition is prepared from the following ingredients:

| | |
|---|---|
| 2-[2-(5-methyl-4-imidazolylmethylthio)ethylamino]-3-nitro-1,4,5,6-tetrahydropyridine | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

The other compounds of Structure 1 can be formulated into pharmaceutical compositions in a similar manner, and these compositions are administered to a subject within the dose ranges given above to block histamine $H_2$-receptors.

We claim:
1. A compound represented by Structure 1:

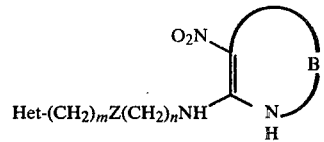

Structure 1 in which
Het is imidazole or pyridine which is attached at a ring carbon and which is optionally substituted by lower alkyl, trifluoromethyl, hydroxymethyl, halogen, hydroxy, lower alkoxy, or amino, provided that when Het is imidazole, the optional substituents do not include hydroxy or amino;
Z is sulphur, methylene or oxygen;
m is 0, 1 or 2 and n is 2 or 3 provided that m+n is 3 or 4; and
B is a 1,2-ethanediyl (—$CH_2$—$CH_2$—) or 1,3-propanediyl (—$CH_2CH_2CH_2$—) group, which group is optionally substituted with one lower alkyl, aryl, aryl lower alkyl or heteroaryl lower alkyl group, aryl being phenyl optionally substituted by lower alkyl, lower alkoxy or halogen and heteroaryl being 2-furyl, 2-thienyl, 2-pyridyl, 3-pyridyl or 4-pyridyl optionally substituted by lower alkyl or lower alkoxy, or a pharmaceutically acceptable acid solution salt thereof.

2. A compound according to claim 1, where $(CH_2)_m$ is linked to a carbon atom of the heterocycle Het adjacent to a nitrogen atom thereof.

3. A compound according to claim 1, where Het is 2- or 4-imidazolyl optionally substituted by lower alkyl, halogen, trifluoromethyl or hydroxymethyl; or 2-pyridyl optionally substituted by lower alkyl, lower alkoxy, halogen, amino or hydroxy.

4. A compound according to claim 3, where Het is 2- or 4-imidazolyl optionally substituted by methyl, chlorine or bromine; or 2-pyridyl optionally substituted by methyl, methoxy, chlorine or bromine.

5. A compound according to claim 1, where Het is 5-methyl-4-imidazolyl, 5-bromo-4-imidazolyl, 3-bromo-2-pyridyl, 3-chloro-2-pyridyl, 3-methoxy-2-pyridyl and 3-hydroxy-2-pyridyl.

6. A compound according to claim 1, which is 2-[2-(5-methyl-4-imidazolylmethylthio)ethylamino]-3-nitro-1,4,5,6-tetrahydropyridine or a pharmaceutically acceptable acid addition salt thereof.

7. A compound according to claim 1, which is 2-[2-(5-methyl-4-imidazolylmethylthio)ethylamino]-3-nitro-4,5-dihydropyrrole or a pharmaceutically acceptable acid addition salt thereof.

8. A pharmaceutical composition to block histamine $H_2$-receptors comprising, in an effective amount to block said receptors, a compound according to claim 1 and a pharmaceutical carrier.

9. A method of blocking histamine $H_2$-receptors which comprises administering an effective amount of a compound according to claim 1 to an animal in need of such treatment.

* * * * *